(12) United States Patent
Ollivier et al.

(10) Patent No.: US 9,804,099 B2
(45) Date of Patent: Oct. 31, 2017

(54) METHOD AND DEVICE FOR THE DETECTION IN PARTICULAR OF REFRACTING DEFECTS

(71) Applicant: TIAMA, Vourles (FR)

(72) Inventors: Michel Ollivier, Acigne (FR); Olivier Colle, Oullins (FR); Marc Leconte, Loire sur Rhone (FR); Florence Drouet, Bures sur Ivette (FR)

(73) Assignee: TIAMA, Vourles (FR)

( * ) Notice: Subject to any disclaimer, the term of this patent is extended or adjusted under 35 U.S.C. 154(b) by 0 days.

(21) Appl. No.: 15/111,493

(22) PCT Filed: Jan. 21, 2015

(86) PCT No.: PCT/FR2015/050144
§ 371 (c)(1),
(2) Date: Jul. 14, 2016

(87) PCT Pub. No.: WO2015/110755
PCT Pub. Date: Jul. 30, 2015

(65) Prior Publication Data
US 2016/0334340 A1 Nov. 17, 2016

(30) Foreign Application Priority Data
Jan. 22, 2014 (FR) .................... 14 50514

(51) Int. Cl.
*G01N 21/90* (2006.01)
(52) U.S. Cl.
CPC .................. *G01N 21/90* (2013.01)

(58) Field of Classification Search
CPC .. G01N 25/72; G01N 21/90; G01N 2021/933; G01N 2021/9063;
(Continued)

(56) References Cited

U.S. PATENT DOCUMENTS 5,004,909 A    4/1991   Fukuchi
6,618,495 B1*  9/2003   Furnas .................. G01N 21/90
                                                 209/526
(Continued)

FOREIGN PATENT DOCUMENTS

FR    2 794 241    12/2000
FR    2 907 553    4/2008
(Continued)

*Primary Examiner* — Sang Nguyen
(74) *Attorney, Agent, or Firm* — Clark & Brody (57) ABSTRACT

A method of inspecting containers (3) moving between a linear camera and a light source (7) presents continuous variation of light intensity with a periodic pattern ($7_1$) along at least one variation direction (D). According to the method, for each movement increment of the container, a sequence of N successive image lines of the container is acquired cyclically so that for each image line; the container (3) is illuminated by the light source (7); the image line of the container is acquired; and the periodic pattern ($7_1$) is shifted for the next line along the variation direction (D). For each increment of the container (3), at least one phase image line is calculated; and the phase image lines (LP(k)) are analyzed.

11 Claims, 4 Drawing Sheets

(58) Field of Classification Search
CPC ... G01N 2021/8832; G01N 2201/0484; G01N 2201/062; B29C 49/80; B29K 2021/00
See application file for complete search history.

(56) References Cited

U.S. PATENT DOCUMENTS

| | | | |
|---|---|---|---|
| 7,697,132 B2* | 4/2010 | Sones | G01N 21/90 250/223 B |
| 7,781,723 B1* | 8/2010 | Furnas | G01N 21/90 209/526 |
| 9,244,020 B2* | 1/2016 | Leconte | G01B 11/06 |
| 9,533,787 B2* | 1/2017 | Kwirandt | B65C 9/067 |
| 9,551,671 B2* | 1/2017 | Colle | G01N 21/90 |
| 2010/0110174 A1* | 5/2010 | Leconte | G01N 21/90 348/92 |

FOREIGN PATENT DOCUMENTS

| | | |
|---|---|---|
| FR | 2 958 040 | 9/2011 |
| FR | 2 958 751 | 10/2011 |
| FR | 2 993 662 | 1/2014 |

* cited by examiner

METHOD AND DEVICE FOR THE DETECTION IN PARTICULAR OF REFRACTING DEFECTS

FIELD OF THE INVENTION

The present invention relates to the technical field of in-line inspection of transparent or translucent containers such as: bottles or flasks, for example, in order to determine characteristics presented by such containers for quality control purposes.

The present invention seeks in particular to inspect containers in order to detect potential defects of the containers, the defects presenting the characteristic of refracting or deflecting light, such as for example defects of the wrinkle, orange peel, rubbing, crinkling, . . . . In the description below, such defects are referred to as refractive defects or as refraction defects.

BACKGROUND ART

In the industrial fabrication of hollow glass containers using known methods such as press-and-blow and blow-blow, it is frequently found that the thickness of glass varies locally in the wall of the container, even for articles that are simple in shape, such as cylindrical bottles. The outside surface that comes into contact with the mold during forming generally has the desired shape. As a result, variations in distribution of glass and thus in wall thickness are manifested by deformation of the inside surface. When such deformation is small, it is of no consequence on the strength or on the appearance of containers. In contrast, poor distribution of material can lead to defective appearance that can sometimes be troublesome, and even worse, it can lead to certain locations where there is no glass. It is considered that a good distribution of glass is a distribution that is of uniform thickness, such that the inside and outside surfaces are substantially parallel throughout. In conventional methods, a poor distribution of glass is characterized and detected by measuring glass thickness, where such measurements are generally point or localized measurements.

In the prior art, various solutions have been proposed for detecting light refracting defects. For example, patent FR 2 794 241 proposes a machine that is adapted to detect refraction defects without turning the container.

That machine includes a conveyor designed to bring containers for inspection up to an inspection station. The inspection station has a camera situated on one side of the conveyor and adapted to take an image of the container. The inspection station also has a light source situated on the other side of the conveyor and associated with means for defining light intensity that varies continuously in cyclic manner in space between dark and bright extremes for the light source, with a rate of change that is less than that needed for detecting defects. Refractive defects of the container have a lens effect, which means that they present to the camera portions of the light source in compressed form. Such a compressed image of the light source with intensity variation at a rate that is greatly increased improves detection of a refractive defect by increasing its contrast.

In practice, that technique is not capable of detecting light refracting defects that have little refracting power.

Another known technique, e.g. as described in U.S. Pat. No. 5,004,909, proposes a device for inspecting the walls of a container, the device comprising a camera for observing a light pattern through a container that is being driven in rotation, which light pattern is made up of alternating white and black stripes. The image of the container is analyzed while taking account of the deformations of the white and black strips due to the presence of a light refracting defect, that can thus be detected.

In practice, that technique is found to be highly sensitive to the distribution of the material constituting the containers. If the glass is distributed in a manner that is not uniform but still acceptable, then the refractions caused by the slope of the inside surface have the effect of greatly deforming the patterns, such that it becomes practically impossible to recognize them, measure them, and analyze them in the images. Consequently, for such productions, it does not appear to be possible to distinguish refracting defects of the containers from irregularities in the wall thickness of the containers. It appears to be possible to detect refracting defects only on productions in which irregularities in the wall thickness of containers are frequent and acceptable.

A method and a device are also known from patent application FR 2 907 553 comprising a light source that is controlled to produce a first type of lighting that is uniform and a second type of lighting that is made up of alternating dark zones and bright zones with discontinuous spatial variation. That device also has means for taking images of articles illuminated by the first and second types of lighting in order to detect respectively high contrast defects and low contrast defects.

Although such a device enables both types of defect to be detected using a single source, that device finds it difficult to detect certain types of refractive defect, mainly because only one image is taken with the second type of lighting. Specifically, high contrast defects are detected with the uniform light source. Additionally, low contrast defects are detected with the single image that is obtained when the source presents alternating black and white stripes with sharp edges and thus with variation that is discontinuous. Deformations of the sharp edges of the striped pattern are analyzed in the image together with local contrast produced by refractive defects, as is done in U.S. Pat. No. 5,004,909. When the container possesses variations in thickness, and thus a poor distribution of glass, the deformations of the pattern are considerable and do not enable low contrast defects to be detected effectively.

Patent application FR 2 958 040 describes a method and an installation for detecting the presence and the extent of defects in an optical component, which method consists in producing a periodic light pattern that is transmitted through the optical component held stationary in an inspection station, in acquiring successive images in transmission through the component of the periodic pattern, which pattern is phase-shifted for each acquisition, in calculating phase images from those successive images, and in analyzing said phase images in order to deduce therefrom the presence of defects.

In practice, that technique is not suitable for in-line inspection of transparent or translucent containers traveling at a high rate between a light source and a system, since it requires the inspected articles to be stopped for a considerable length of time in order to acquire a plurality of images.

SUMMARY OF THE INVENTION

The present invention thus seeks to remedy the drawbacks of the prior art by proposing a novel technique for in-line inspection of transparent or translucent containers, the technique being suitable for detecting at least light refracting defects, independently of the uniformity of material distribution.

Another object of the invention is to propose a method enabling containers traveling in-line at high speed to be inspected in order to detect, with great reliability, at least light refracting defects and also at least to determine the quality of the distribution of the material constituting the containers.

The present invention seeks to propose a method of in-line optical inspection of transparent or translucent containers traveling at a high rate between a linear camera and a light source presenting continuous variation in light intensity with a periodic pattern of spatial period along at least one variation direction, the light source and the linear camera being connected to a control and image processing unit.

According to the invention, the following steps are performed:

- for each movement increment of the inspected container, a sequence of N successive image lines of the container is acquired cyclically for $i$ lying in the range 1 to N, where N is not less than 3, such that for each image line, the following steps are performed:
  - illuminating the container with the light source;
  - acquiring the image line of the container; and
  - shifting the periodic pattern for the next line in the variation direction through a distance;
- for each increment of the container, calculating at least one phase image line from the N image lines; and
- analyzing the phase image lines in order to deduce therefrom as a characteristic of the container, at least the presence of a light refracting defect or the quality of the distribution of the material constituting the container.

In addition, the method of the invention may also present in combination one or more of the following additional characteristics:

- the analysis of the phase image lines consists in determining the speed and/or the amplitude of local phase variation and in comparing said speeds and/or amplitudes with thresholds in order to determine the presence of a light refracting defect or the quality of the distribution of the material constituting the container;
- for analyzing the phase image lines, and after the operation seeking to obtain phase image lines for each container, it includes an operation of phase unfolding;
- for each movement increment of the container, using the N image lines to calculate at least one light intensity image line;
- juxtaposing the light intensity image lines that are obtained for successive movement increments so as to obtain a transmission image of the container or of a portion of the container;
- analyzing the transmission image containing the information about the quantity of light transmitted by the container in order to deduce therefrom as a characteristic of the container, at least the presence of a light absorbing defect;
- the variation direction of the periodic pattern is parallel, perpendicular, or oblique relative to the sensor array of the linear camera;
- for analyzing phase image lines, the method consists in juxtaposing image lines or phase image lines or unfolded phase image lines obtained for successive movement increments so as to obtain a phase image of at least a portion of the container; and
- the analysis of the phase image lines includes a geometrical correction step in order to reduce the effects of vibration of the container during its movement and/or the effects of perspective due to observation being non-orthogonal relative to the movement direction.

The invention also seeks to provide an optical device for high throughput inspection on a production line of transparent or translucent containers moving between a linear camera and a light source presenting continuous variation of light intensity with a periodic pattern of spatial period in at least one variation direction, the light source and the linear camera being connected to a control and image processing unit.

According to the invention:

- the light source is suitable for presenting continuous variation of intensity between a dark light level and a bright light level with a periodic pattern of spatial period in at least one intensity variation direction; and in that
- the control and image processing unit:
  - acquires from the linear camera a sequence of N successive image lines of the container for each movement increment, for $i$ varying from 1 to N, with N not less than 3, and repeating the following operations for each image line:
    - controlling the light source so that the periodic pattern presents the periodic variation of light intensity in a position;
    - acquiring the line of the container; and
    - causing the periodic pattern to be shifted for the next line along the variation direction through a distance, in order to take the position;
  - calculates, for each increment of the container, at least one phase image line on the basis of the N image lines; and
  - analyzes the phase image line in order to deduce therefrom as a characteristic of the container, at least the presence of a light refracting defect or the quality of the distribution of the material constituting the container.

In addition, the device of the invention may also present in combination at least one or more of the following additional characteristics:

- the light source comprises a set of individual light sources possibly situated behind a diffusing panel and controlled individually or by independent groups, the signals coming from the control unit enabling individual sources to be switched on, and for each individual source and for each integration period of the linear camera, the signals from the control unit enabling a lighting time or voltage or current to be controlled so as to modulate the intensity of light emitted during the camera integration time;
- the light source comprises N individual light sources that are switched on one by one, each presenting, when switched on, light variation with the same periodic pattern of spatial period in at least one variation direction, but offset between the light sources in the variation direction through a distance, and an optical device that mixes the N sources so that the only perceptible difference from the point of view of the camera when lighting is switched on from one source to another, is the shifting of the pattern along the variation direction; and
- the control and processing unit is connected to:
  - a system of sensors for taking account of the travel speed or rotation speed of the containers in order to adapt the reading speed of the camera and the display speed of the various patterns of the light source; and/or
  - to an ejector device for ejecting defective containers; and/or to a computer system for supervision, for counting defects, or for measuring distributions of glass.

BRIEF DESCRIPTION OF THE DRAWINGS

Various other characteristics appear from the following description made with reference to the accompanying drawings, which show embodiments of the invention as non-limiting examples.

DETAILED DESCRIPTION OF THE DRAWINGS

Figure 1:
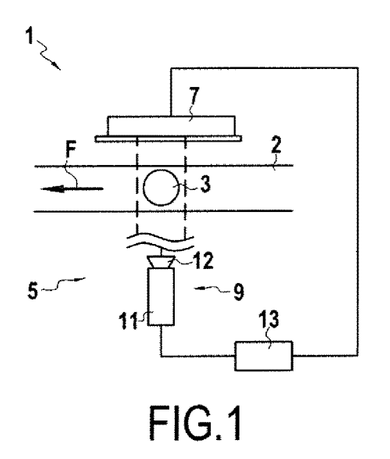
FIG. 1 is a plan view of a machine for inspecting containers that are moving in translation, the machine performing the method in accordance with the invention.

As can be seen in FIG. 1, the inspection machine 1 of the invention includes mover means 2 for moving transparent or translucent containers 3 along a path designated by arrow F, i.e. a linear horizontal travel direction in the example shown in FIG. 1. The containers 3 are transported while in an upstanding or upright position at a high rate, i.e. typically 50 to 600 articles per minute, i.e. traveling at a speed that may be as great as 1.2 meters per second (m/s). The containers 3 are thus caused to travel in succession at a high rate past an inspection station 5.

Figure 2:
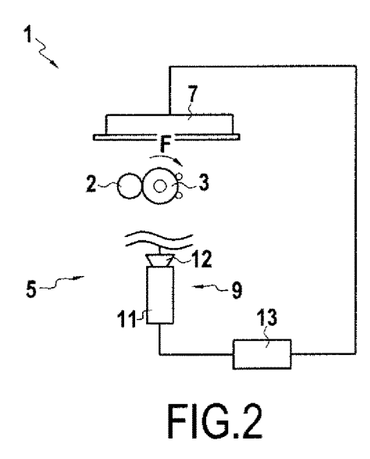
FIG. 2 is a plan view of a machine for inspecting containers that are moving in rotation, the machine performing the method in accordance with the invention.

FIG. 2 is a view of a machine 1 for inspecting containers 3 that are driven in rotation along a circular path F. Conventionally, each container 3 is driven in rotation about its own vertical axis of symmetry Y through at least one revolution by mover means 2 of any known type. The containers 3 are brought automatically in succession to the inspection station 5 and taken away therefrom using any conventional means.

Figure 3:
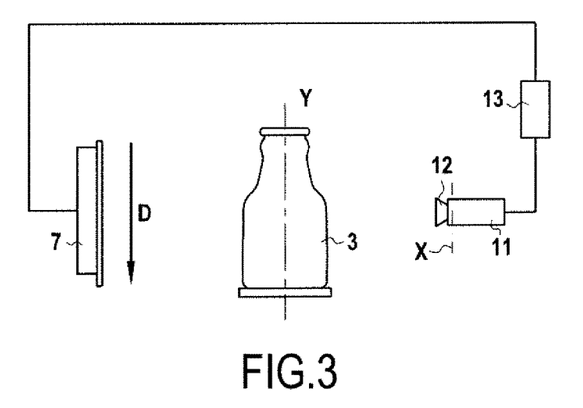
FIG. 3 is a profile view of the machine in accordance with the invention.

The inspection station 5 includes at least one light source 7 arranged on one side of the container 3, and a system 9 for taking images of the containers that is arranged on the other side of the container 3. Thus, as can be seen more precisely in FIGS. 1 to 3, each container 3 is caused to move between the light source 7 and the system 9 taking images of the containers 3 in association with the light source 7.

The image-taking system 9 comprises a linear camera 11 with a lens 12 that is connected to a unit 13 for providing control and for processing the images taken. The control and processing unit 13 serves to take images of the containers and analyze them in order to deduce at least one characteristic of each container. As explained in detail below in the description, this control and processing unit 13 is capable of deducing, as a characteristic of the containers, the presence of a light refracting defect and/or the quality with which the material constituting the container is distributed.

According to a characteristic of the invention, the camera 11 is of the linear type, i.e. it delivers a single line of pixels extending in a rectilinear direction X. The linear camera may take pictures in color or in black and white, it may be sensitive to ultraviolet, visible, or infrared light, and by way of example it may be of the time shifting and integrating type. Linear cameras provide high resolution at a reasonable price, and in particular resolution in the range 1024 to 4096 pixels. Nevertheless, the speed at which the linear camera is read is very high, reaching 40 kilohertz (kHz), which is much greater than the frequency with which a matrix camera using the same technology can be read, for example.

The linear camera 11 possesses an observation field that is adapted to cover a portion of the container 3. Advantageously, the camera 11 is adapted to take images of a container 3 over its entire height. For this purpose, the light source 7 has a light-emitting surface of sufficient extent to backlight at least a portion of the observed field corresponding to the zone of the container that is to be inspected, and in particular the wall of the container along its entire height. It should be observed that the inspection station 5 may have a plurality of image-taking systems combined with light sources to enable containers to be inspected over all or part of their circumference as they move past the inspection station 5.

It should be observed that when the movement of the containers 3 is movement in translation along a determined direction F, then the direction X of the sensor array of the linear camera 9 is not parallel to the travel direction F. When the movement of the containers 3 is rotation about the vertical axis of symmetry Y of each container 3, then the direction X of the sensor array of the linear camera 9 is not perpendicular to the vertical axis of symmetry Y of each container 3.

According to a characteristic of the invention, the light source 7 presents continuous variation in light intensity with a periodic pattern $7_1$ that is adapted to be transmitted through the container 3. Thus, the periodic light pattern $7_1$ is seen through the container 3, by transmission. The light source 7 presents a periodic light intensity pattern of spatial period T, along at least a first variation direction D. The periodic light pattern $7_1$ of the light source as shown by way of example in FIGS. 4 and 5 corresponds to spatial variation in the emitted light intensity. Thus, different points of the light source 7 emit more or less light.

The variation in light intensity (or overall contrast) of the light source 7 may extend from a determined dark level to a determined bright level, at least along the first variation direction. In this first direction D, this variation in light intensity is a periodic function, e.g. a function that is quasi-sinusoidal and that is preferably sinusoidal. Providing it can be reproduced without change of form on being shifted, it is possible to use a non-sinusoidal periodic function, even though that presents the drawback of making phase calculation more complex and/or requiring a greater number of images to be acquired, thereby making the use of the invention for in-line inspection of transparent or translucent containers more expensive.

When the periodic variation of the light source 7 is not strictly sinusoidal, the processing of the image may remain the same, i.e. it may have a step of calculating a phase image on the assumption that the variation is sinusoidal. This leads to local errors in determining phase, and the phase shift values are not strictly exact. This means that it is not possible to measure the three-dimensional shapes of the surfaces or interfaces through which light passes, but that is in any case limited by the fact that light passes through four interfaces. However it remains possible with good discrimination capacity to detect refractive defects and/or glass distribution defects, insofar as only strong local variations of phase are to be detected (i.e. variations that are fast and/or of large amplitude), which is the main purpose of the invention.

According to a preferred implementation characteristic, the periodic pattern $7_1$ presents light intensity variation in the variation direction D that is sinusoidal. In the example shown in FIG. 4, the variation direction D is parallel to the vertical axis of symmetry Y of the containers 3, whereas in the example shown in FIG. 5, the direction of variation D is perpendicular to the vertical axis Y of the containers 3. In these examples, the intensity or brightness values of the source along the direction D vary between a minimum (Lo−A) and a maximum (Lo+A) in application of the formula:

$$L(x) = Lo + A \sin(\omega \cdot x + \varphi)$$

where:
L(x): light intensity emitted for abscissa point $\underline{x}$;
Lo: mean intensity;
A: amplitude of variation;
ω: angular frequency;
φ: phase at x=0.

Figure 4:
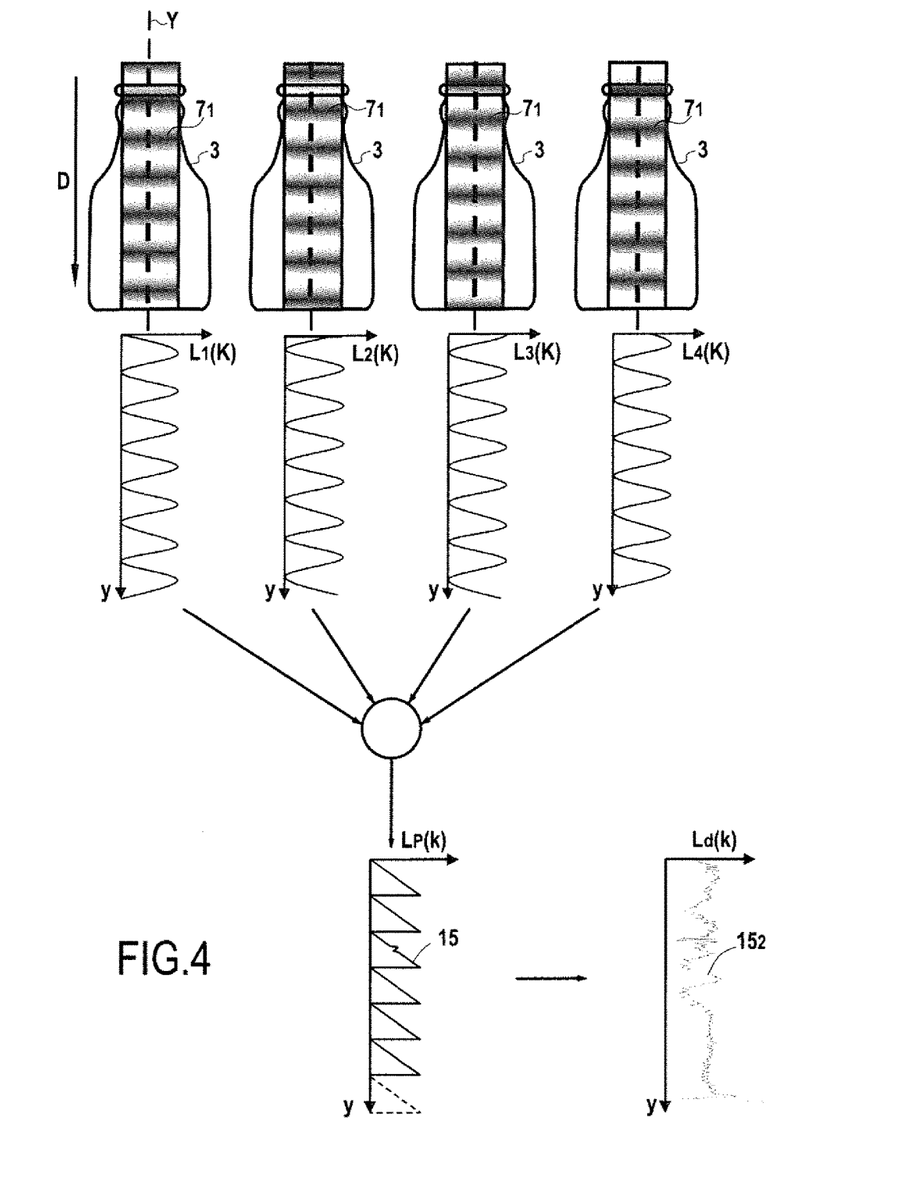
FIG. 4 shows a sequence of four image lines obtained for a movement increment of the container while a container is being illuminated with a light pattern that is shifted for each image line, and in which the variation in light intensity is parallel to the vertical axis of the container.
Figure 5:
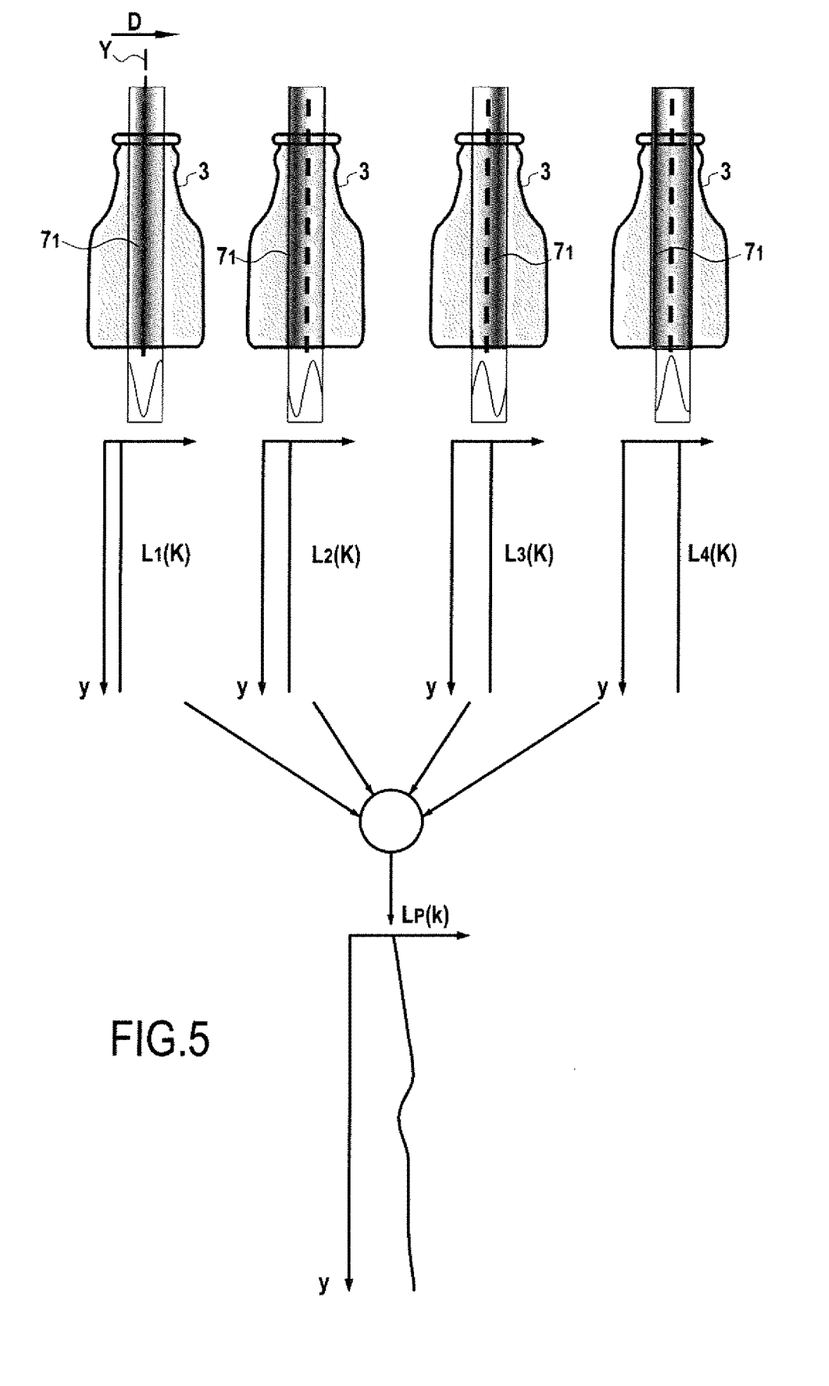
FIG. 5 shows a sequence of four image lines obtained for a movement increment of the container while a container is being illuminated by a light pattern that is shifted for each image line and in which the variation in light intensity is perpendicular to the vertical axis of the container.

In the examples shown in FIGS. 4 and 5, the periodic light pattern $7_1$ presents a structure of rectilinear light fringes. In FIGS. 4 and 5, the light source 7 presents light intensity variation with the periodic pattern, having a maximum in the direction D and zero in the direction perpendicular to the direction in which the rectilinear light fringes extend.

In the description below, the light intensity variation direction D is considered relative to horizontal and vertical directions taken in a 0, $\underline{x}$, $\underline{y}$ reference frame. In the shown in FIG. 4, the light intensity variation direction D of the light source 7 corresponds to the maximum variation of light intensity, which is vertical (axis $\underline{y}$), such that in the horizontal direction (axis $\underline{x}$), the light intensity of the light source is constant. In the example shown in FIG. 5, the light intensity variation direction D of the light source 7 is shown as being parallel relative to the horizontal direction (axis $\underline{x}$). It should be observed that the direction of maximum variation in the light intensity of the light source may present an angle of inclination α relative to the horizontal direction (axis $\underline{x}$). Thus, the variation direction D of the periodic pattern may be parallel, perpendicular, or oblique relative to the direction of the sensor array of the linear camera.

In the examples shown in FIGS. 4 and 5, the light source 7 presents an array of light fringes that are parallel to a single direction. It should be observed that it is possible to envisage the light source 7 presenting fringes in a plurality of directions. Thus, the light source 7 may present fringes of other shapes, such as shapes that are curved, concentric circles, chevrons, etc. These complications to the light pattern present the advantage of adapting detection sensitivity in different regions of the article, considering that detection is anisotropic because of the way the pattern is oriented.

The light source 7 is selected essentially as a function of the nature of the container characteristics that are to be determined, and as a function of the shape of the containers, as can be understood from the description below.

According to an advantageous characteristic of the invention, it should be observed that the inspection station 5 may have a plurality of light sources 7 with periodic patterns presenting light intensity variations that extend in different directions.

The control and processing unit 13 controls the light source 7 and the camera 11 so as to acquire a sequence of successive images for each container 3 placed in front of the light source 7, which acquisition is repeated cyclically for each movement increment of the container, written $\underline{k}$ in the description below. For each movement increment $\underline{k}$, the container 3 occupies a different position along the travel path F. In practice, the containers 3 move continuously in front of the camera 11, and the travel increments correspond to different positions of the container along its travel path F. Given that the images are acquired by a linear camera 11, the images that are taken are referred to in the description below as image lines Li(k) of the container, for $\underline{i}$ varying over the range 1 to N.

According to a characteristic of the invention, for each movement increment $\underline{k}$, the control and image processing unit acquires from the linear camera a sequence of N successive linear images referred to as image lines Li(k) of the container for $\underline{i}$ varying from 1 to N, where N is greater than 2, i.e. not less than 3, giving L1(k) to LN(k). Such a sequence of N image lines for a movement increment is taken in such a manner that, for each image line Li(k):
- the container 3 is illuminated by the light source 7;
- the image line Li(k) of the container is acquired; and
- the periodic pattern $7_1$ is shifted for the next line Li+1(k) in the variation direction D through a distance T/N, with the spatial period of the light pattern.

In the example shown in FIGS. 4 and 5, for each movement increment $\underline{k}$, a sequence of four illuminations is created with the light source with the periodic pattern $7_1$ being shifted along the variation direction D through a distance T/4. For each of these illuminations, four image lines L1(k), L2(k), L3(k), and L4(k) are acquired in the example shown, taken on the dashed lines in FIGS. 4 and 5.

Between each acquisition of an image line of a sequence, there is a relative spatial shift along the periodic pattern variation direction D between the container 3 and the periodic pattern $7_1$ from the light source 7. Thus, for each sequence, the periodic pattern $7_1$ is shifted in the variation direction D from one image to the next past the container 3, which is considered as being stationary.

Specifically, it can be considered that the movement of the container 3 is negligible between two successive acquisitions. It can thus be assumed that N successive reads correspond to reads of the same portion of the container. For example, for containers traveling at 1 m/s, a 40 kHz camera reads 40 lines per millimeter (mm). For example, four successively acquired image lines (the pattern of the light source being shifted on each occasion) may be considered as being four reads on the container of the same image line having a width of 0.1 mm.

The periodic pattern of the light source 7 may be shifted in any appropriate way. Thus, the light source 7 may comprise a set of individual light sources, possibly situated behind a light diffusing panel, and controlled independently or as independent groups, the signals coming from the control unit serving to cause the individual light sources to be switched on and making it possible, for each individual light source and for each integration period of the linear camera, to control the time the source is on or a voltage or a current so as to modulate the light intensity that is emitted during the integration time of the camera.

Figure 6A:
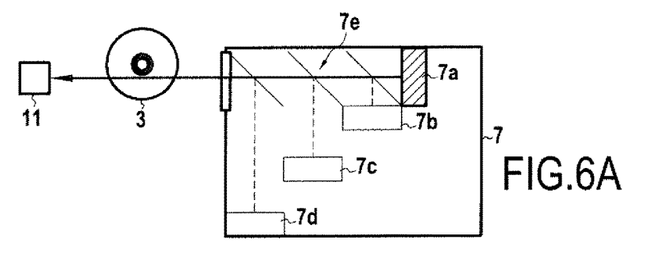
FIGS. 6A and 6B are examples showing the operation of successive independent light sources making up a light source in accordance with the invention.
Figure 6B:
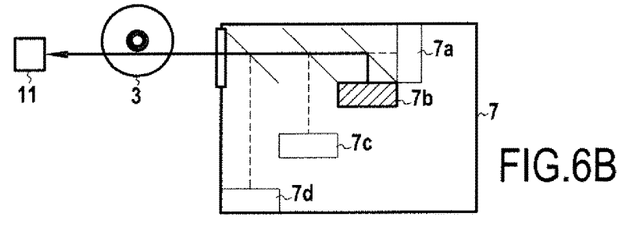

In another implementation shown in FIGS. 6 and 6A, the light source 7 comprises N (four in the example shown) independent light sources 7a, 7b, 7c, 7d suitable for being switched on one by one and each presenting, when switched on, light variation having the same periodic pattern $7_1$ of spatial period T along at least one variation direction D, but with a shift through a distance T/N between the sources along the variation direction D. The light source 7 also has an optical device 7e that mixes the N sources so that the only difference that can be perceived from the viewpoint of the camera 11 when switching one or another independent source is the shifting of the periodic pattern along the variation direction D. In the example shown, the optical device 7e comprises semi-reflecting optical plates picking up the light beams delivered by the independent light sources.

The control and processing unit 13 acquires a sequence of at least three image lines L1(k) to LN(k) in transmission through each container 3 using the camera 11, and for each movement increment, each image line presenting a shift of its periodic pattern relative to the container along a periodic pattern variation direction D. Thus, for each movement increment, the control and processing unit 13 has at least three image lines in which the periodic pattern is phase-shifted relative to the container.

The control and processing unit 13 then uses the N image lines L1(k) to LN(k) to construct at least one phase image line LP(k) for each container and for each movement increment $\underline{k}$ of the container 3. For each point of the container, the variation in its gray level in the N image lines is known and corresponds to the relative shift of the periodic pattern. It is thus possible to calculate the phase of each point of the container. The phase image lines may be calculated using various techniques, and in particular in accordance with patent EP 1 980 843, for example.

It is necessary to acquire at least three image lines L1(k), L2(k), and L3(k) in order to obtain a phase calculation for each pixel of the phase image line LP(k). Specifically, when the pattern is considered to be sinusoidal, the shift of the pattern between each acquisition gives rise, for each pixel of the camera, to a time variation in its gray level, and this function of time is likewise sinusoidal. At least three values need to be known of a sinewave in order to determine it and thus discover its phase. The phase of each pixel along the line LP(k) is thus determined by having knowledge of at least three values during the phase shifting of the pattern. If light is not deflected by the container being inspected, then the phase as determined in this way is constant for all of the pixels along the line LP(k), which can happen for example when there is no container interposed between the light source and the camera, or indeed when the container is constituted by surfaces that are plane and parallel. Conversely, if the container for inspection has locations that deflect the light passing through it, then phase variations are caused along the lines LP(k) at the locations of these deflections. Having knowledge of a greater number of values (N>3) enables a sinewave to be determined more accurately in the presence of noise or of various disturbances, either by discarding erroneous values, or by performing regressions of higher order. Thus, by increasing the number N of images LN(k) that are acquired, for each movement increment $\underline{k}$, a phase image line LP(k) can be obtained that, theoretically is of better quality. Nevertheless, in the invention, for a given minimum reading time (Ti) of the linear camera, acquiring a larger number N of lines LN(k) would require a longer acquisition duration for these N images, such that the movement of the containers during the duration (N×Ti) would no longer be negligible. That would lead to a drop in the resolution of the system, or to a limit on the throughput rate of the system, or indeed to erroneous phase image lines LP(k). Advantageously, the number of image lines that are acquired for each movement increment lies in the 3 to 5. For example, when N is 5, using a camera operating at a line frequency of 50 kHz (50,000 lines acquired per second), and for containers traveling on a conveyor at a speed of 1 m/s, the movement increment is 0.1 mm, and thus the resolution of the phase image IP in the travel direction is 10 pixels per millimeter.

From N image lines acquired for each movement increment of each container, the phase image LP(k) is calculated as mentioned above (FIGS. 4 and 5). For each container, the control and processing unit 13 has at least one and more generally a plurality of N image lines, each made up of N lines Li(k) for i=1 to N, with a cyclic shift of the pattern of the source for each value of $\underline{i}$, and with continuous or incremental movement of the article for each value of $\underline{k}$. A phase calculation algorithm is applied individually to each point of the container. Which phase calculation algorithm is selected from among the various algorithms that are available depends in particular on the container, on the periodic pattern, on the speed of calculation, on the desired accuracy, etc.

In a variant of the invention, the method of analyzing phase image lines LP(k) comprises, after the operation of obtaining phase image lines for each container, an operation of phase unfolding. Specifically, and given the periodicity of the light source 7, the phase that is obtained is also periodic so as to be defined solely in the range $-\pi$ to $\pi$. It is possible to envisage unfolding phase in order to avoid $2\pi$ discontinuities when obtaining the phase variation information Ld(k). As shown in FIG. 4, when the direction D is parallel to the image lines delivered by the camera, the phase obtained in the phase line LP(k) varies periodically and presents discontinuities of amplitude $2\pi$. A refractive defect 15 can be identified in the signal Lp(k). After unfolding, the defect $15_2$ is to be found in the unfolded phase Ld(k). FIG. 7B shows this example of said unfolded phase image Ld(k) relative to the position of the defect in a two-dimensional unfolded phase image obtained firstly by juxtaposing lines for successive values of $\underline{k}$ and secondly by unfolding phase.

The control and processing unit 13 then serves to analyze each phase image line and more precisely to analyze phase variations in order to deduce therefrom at least one characteristic of the container 3. In a first variant implementation, analysis of the phase image line consists in determining the speed and/or the amplitude of the variation of the signal in the phase image line and in comparing the speeds and/or amplitudes with thresholds in order to determine that a light refracting defect is present or the quality with which the material constituting the container is distributed. The processing of each phase image line may be performed using various known methods. For example, provision may be made to detect local phase variations (or shifts), e.g. by comparing the phase of each point of the image line with the phase of neighboring points. Another technique consists in calculating, for each point, a phase variation slope and in comparing the result at each point with a threshold value. This variation slope can be calculated in one or more appropriate directions.

If phase variation is fast and of amplitude greater than a given threshold, it is then possible to deduce at least one characteristic of the container, namely the presence of a light refracting defect. If the phase variation is slow and of amplitude greater than a given threshold, it is then possible to deduce at least one other characteristic of the container, namely poor distribution for the material constituting the container.

In a second variant implementation, frequency analysis of the phase image is performed in order to select variations as a function of their spatial frequency and thus detect the presence of refractive defects and possibly even qualify the skin quality of the glass by the amplitude of high frequencies, and the quality of material distribution by the amplitude of low frequencies.

The phase variations depend directly on light being deflected or refracted by the container under the effect of refracting defects and of the distribution of glass.

In a variant of the invention, the control and processing unit 13 calculates a phase image line LP(k) directly for each sequence of N image lines Li(k), i=1 to N, and it analyzes each of said phase lines LP(k) separately performing unfolding and then searching for defects. This is possible when the direction D is not orthogonal to the image line, since it is then possible to unfold phase. At this stage, it is possible either to detect the defects in the unfolded image lines, or to juxtapose the unfolded phase image lines that are obtained for successive movement increments (k) so as to obtain a two-dimensional unfolded phase image, which can then be analyzed.

In an advantageous implementation, that operates regardless of the direction D relative to the image line, the control and processing unit 13 calculates a phase image line LP(k) for each sequence of N image lines Li(k), i=1 to N, and it then juxtaposes the phase image lines LP(k) obtained for successive movement increments $\underline{k}$ in order to constitute a phase image IP of at least a portion of the container, said phase image then being analyzed. Insofar as the invention makes it possible to superpose exactly (pixel on pixel) N image lines Li(k), it is naturally equivalent for analyzing phase image lines LP(k), for the control and processing unit 13 to juxtapose image lines Li(k) obtained for successive increments $\underline{k}$ in N two-dimensional images, each corresponding to one of the N shift positions of the pattern, and then combine the N two-dimensional images in order to calculate the phase image IP of at least a portion of the container, said phase image then being analyzed.

Thus, in general manner, for analyzing the phase image lines LP(k), the method consists in juxtaposing image lines Li(k) or phase image lines LP(k) or unfolded phase image lines, obtained for successive movement increments $\underline{k}$ in such a manner as to obtain a phase image IP of at least a portion of the container. The juxtaposition of image lines making it possible to obtain and analyze two-dimensional images is preferably performed at the latest prior to unfolding phase, such that this step then takes account of information that is more complete.

Figure 7A:
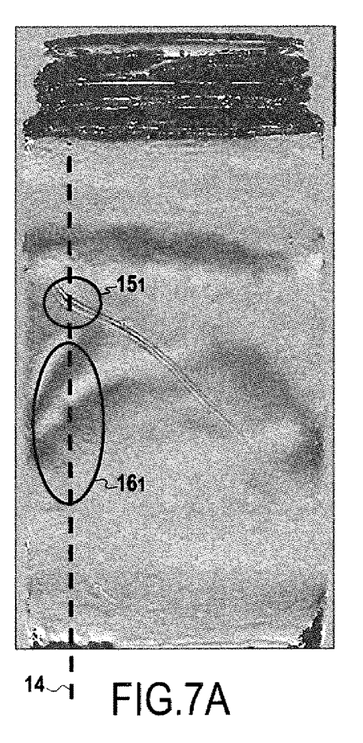
FIG. 7A shows an example of an unfolded phase image serving to reveal a light refraction defect.
Figure 7B:
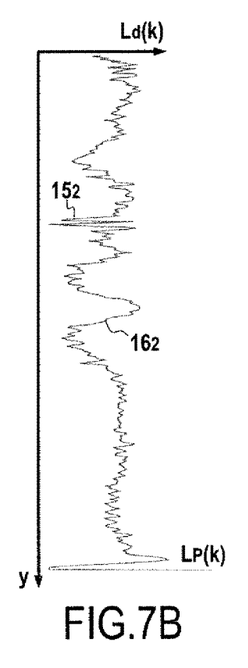
FIG. 7B shows the values of the signal for the image shown in FIG. 7A and taken along the line of the image, as represented by reference 14.

FIG. 7A shows an example of an unfolded phase image, e.g. by differentiating the phase image IP, serving to reveal a light refracting defect. In this image of FIG. 7A, the reference $15_1$ designates the presence of a wrinkle on the container. Reference $16_1$ shows slow variations of phase due to light being deflected by non-uniform distribution of the glass and it is revealed by regions that are bright and dark.

The refractive defect, namely the wrinkle $15_1$ in the example shown, is easily located by its signature $15_2$ that appears in the signal of the unfolded phase image line shown in FIG. 7B that corresponds to the column in the image given reference 14. The refractive defect gives rise to steep slopes of local variation in the signal. In this signal of the unfolded phase image line taken on the line 14, there can also be seen slow variations associated with the non-uniform distribution of glass, these slow variations being identified by the reference $16_2$ in the signal of FIG. 7B.

Figure 7C:
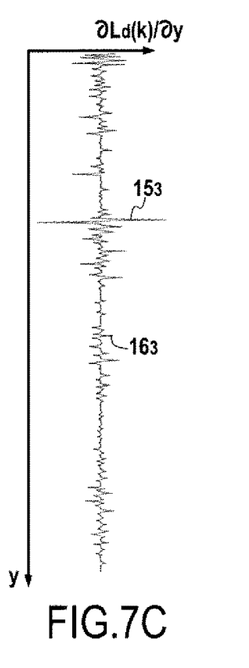
FIG. 7C shows an example of the result of processing the signal shown in FIG. 7B by means of a high-pass filter.

FIG. 7C shows by way of example the result ∂LP(k)/∂y of processing the unfolded phase image line shown in FIG. 7B using a high-pass filter in the form of a partial derivative in the direction D, which in this example is equal to the direction Y. The defect $15_1$ that can be seen in the image line of FIG. 7A is easily detectable in the signal shown in FIG. 7C (reference $15_3$) since the amplitude of local variations in the signal is strong.

In the signal shown in FIG. 7C, reference $16_3$ identifies slow variations associated with the non-uniform distribution of glass. It should be observed that the non-uniform nature of the distribution of glass does not spoil the detection of the refracting defect since this non-uniform distribution of glass does not produce significant modifications to the signal, as can be seen in the vicinity of the reference $16_3$.

It should be considered that the periodic pattern $7_1$ is observed through the containers and thus for the central zone through four successive interfaces: air-glass, glass-air, air-glass, and glass-air, corresponding respectively to four surfaces: outside, inside, inside, and outside through which the light passes. Since these surfaces are not uniformly mutually parallel, given the non-uniform distribution of the material and the presence of surface defects, bubbles, etc., they deflect light like prisms. The periodic light pattern $7_1$ is thus deformed when observed through the transparent container. Unlike techniques that seek to detect only deformations in patterns and the appearance within such patterns of points or zones of local contrast, the phase shift method enables phase to be calculated, thereby providing a measurement of the deflections to which light rays have been subjected, thus making it possible to perform fine and discriminating analysis enabling the refracting power of defects to be characterized and enabling the quality of material distribution to be characterized.

In the above-described examples, provision is made to illuminate each container using a light source that presents light intensity variation in a variation direction D. In another variant implementation, it should be observed that it is possible to envisage illuminating each container using a light source that presents light intensity variation with a periodic pattern of period $T_2$ in a second variation direction that is different from the first variation direction D.

According to an advantageous implementation characteristic, the control and processing unit 13 controls the light source 7. The control and processing unit 13 controls the light source 7 so that the periodic light pattern $7_1$ is shifted in a given direction for each acquisition of an image line by the linear camera, as explained above.

According to an implementation characteristic, the control and processing unit 13 triggers acquisitions as a function of the precise position of the container in front of the light source. For this purpose, the control and processing unit 13 may be connected to sensors for sensing presence and/or movement, such as incremental coders and cells.

In a second embodiment of the inspection station, the control and processing unit 13 also has means for calculating at least one intensity image from N image lines of each sequence of the container coming from the image-taking system 9. In an advantageous implementation variant, these light intensity image lines that are obtained for $\underline{k}$ successive movement increments are juxtaposed so as to obtain a transmission image of the container or of a portion of the container. The control and processing unit 13 also has means for analyzing intensity images or the transmission image in order to deduce therefrom, as a characteristic of the container 3, the presence of a defect that absorbs light, and/or the dimensions of the container.

In conventional manner, the control and processing unit 13 is connected to:
- a system of sensors in order to take account of the travel speed or speed of rotation of the containers 3 in order to adapt the reading speed of the camera and the speed at which the various patterns of the light source 7 are displayed; and/or
- an ejector device for ejecting deflective containers; and/or
- a computer system for providing supervision, for counting defects, or for measuring distributions of glass.

According to an advantageous implementation characteristic, the linear camera delivers the image lines Li(k) at a frequency that varies as a function of measuring the travel speed of the containers so that the spatial resolution of the phase images IP is constant.

According to another advantageous implementation characteristic, analysis of the phase image lines LP(K) includes a geometrical correction step for reducing the effects of the container vibrating while it moves and/or for reducing the effects of perspective due to observation not being orthogonal to the travel direction.

The invention is not limited to the examples described and shown, since various modifications may be made thereto without going beyond its ambit.

The invention claimed is:

1. A method of in-line optical inspection of transparent or translucent containers (3) traveling at a high rate between a linear camera (11) and a light source (7) presenting continuous variation in light intensity with a periodic pattern (7$_1$) of spatial period (T) along at least one variation direction (D), the light source and the linear camera (11) being connected to a control and image processing unit (13), said method being characterized by the following steps:
   for each movement increment ($\underline{k}$) of the inspected container, a sequence of N successive image lines (Li(k)) of the container is acquired cyclically for $\underline{i}$ lying in the range 1 to N, where N is not less than 3, such that for each image line (Li(k)), the following steps are performed:
      illuminating the container (3) with the light source (7);
      acquiring the image line (Li(k)) of the container; and
      shifting the periodic pattern (7$_1$) for the next line (Li+1(k)) in the variation direction (D) through the distance (T/N);
   for each increment ($\underline{k}$) of the container (3), calculating at least one phase image line (LP(k)) from the N image lines (L1(k) to LN(k)); and
   analyzing the phase image lines (LP(k)) in order to deduce therefrom as a characteristic of the container (3), at least the presence of a light refracting defect or the quality of the distribution of the material constituting the container.

2. A method according to claim 1, characterized in that the analysis of the phase image lines (LP(k)) consists in determining the speed and/or the amplitude of local phase variation and in comparing said speeds and/or amplitudes with thresholds in order to determine the presence of a light refracting defect or the quality of the distribution of the material constituting the container.

3. A method according to claim 1, characterized in that for analyzing the phase image lines (LP(k)) and after the operation seeking to obtain phase image lines for each container, it includes an operation of phase unfolding.

4. A method according to claim 1, characterized by the following steps:
   for each movement increment ($\underline{k}$) of the container (3), using the N image lines (L1(k) to LN(k)) to calculate at least one light intensity image line (LT(k));
   juxtaposing the light intensity image lines (LT(k)) that are obtained for successive movement increments ($\underline{k}$) so as to obtain a transmission image of the container or of a portion of the container; and
   analyzing the transmission image containing the information about the quantity of light transmitted by the container in order to deduce therefrom as a characteristic of the container (3), at least the presence of a light absorbing defect.

5. A method according to claim 1, characterized in that the variation direction (D) of the periodic pattern is parallel, perpendicular, or oblique relative to the sensor array of the linear camera.

6. A method according to claim 1, characterized in that, for analyzing phase image lines (LP(k)), it consists in juxtaposing image lines (Li(k)) or phase image lines (LP(k)) or unfolded phase image lines obtained for successive movement increments ($\underline{k}$) so as to obtain a phase image (IP) of at least a portion of the container.

7. A method according to claim 1, characterized in that the analysis of the phase image lines (LP(K)) includes a geometrical correction step in order to reduce the effects of vibration of the container during its movement and/or the effects of perspective due to observation being non-orthogonal relative to the movement direction.

8. An optical device for high throughput inspection on a production line of transparent or translucent containers (3) moving between a linear camera (11) and a light source (7) presenting continuous variation of light intensity with a periodic pattern of spatial period (T) in at least one variation direction (D), the light source (7) and the linear camera (9) being connected to a control and image processing unit (13), the device being characterized in that:
   the light source (7) is suitable for presenting continuous variation of intensity between a dark light level and a bright light level with a periodic pattern (7$_1$) of spatial period (T) in at least one intensity variation direction (D); and in that
   the control and image processing unit:
      acquires from the linear camera a sequence of N successive image lines (Li(k)) of the container for each movement increment ($\underline{k}$), for $\underline{i}$ varying from 1 to N, with N not less than 3, and repeating the following operations for each image line (Li(K)):
         controlling the light source (7) so that the periodic pattern (7$_1$) presents the periodic variation of light intensity in a position (Pi);
         acquiring the line (Li(k)) of the container; and
         causing the periodic pattern (7$_1$) to be shifted for the next line (Li+1(k)) along the variation direction (D) through a distance (T/N), in order to take the position (Pi+1);
      calculates, for each increment ($\underline{k}$) of the container (3), at least one phase image line (LP(k)) on the basis of the N image lines (L1(k) to LN(k)); and
      analyzes the phase image line (LP(k)) in order to deduce therefrom as a characteristic of the container (3), at least the presence of a light refracting defect or the quality of the distribution of the material constituting the container.

9. A device according to claim 8, characterized in that the light source (7) comprises a set of individual light sources possibly situated behind a diffusing panel and controlled individually or by independent groups, the signal coming from the control unit enabling individual sources to be switched on, and for each individual source and for each integration period of the linear camera, the signals from the control unit enabling a lighting time or voltage or current to be controlled so as to modulate the intensity of light emitted during the camera integration time.

10. A device according to claim 8, characterized in that the light source (7) comprises N individual light sources (7a, 7b, 7c, . . . ) that are switched on one by one, each presenting, when switched on, light variation with the same periodic pattern (7₁) of spatial period (T) in at least one variation direction (D), but offset between the light sources in the variation direction (D) through a distance (T/N), and an optical device (7e) that mixes the N sources so that the only perceptible difference from the point of view of the camera when lighting is switched on from one source to another, is the shifting of the pattern along the variation direction (D).

11. A device according to claim 8, characterized in that the control and processing unit (13) is connected to:
- a system of sensors for taking account of the travel speed or rotation speed of the containers in order to adapt the reading speed of the camera and the display speed of the various patterns of the light source (7); and/or
- to an ejector device for ejecting defective containers; and/or
- to a computer system for supervision, for counting defects, or for measuring distributions of glass.

* * * * *